(12) United States Patent
Santangelo

(10) Patent No.: US 6,627,659 B1
(45) Date of Patent: Sep. 30, 2003

(54) METHODS OF DECREASING THE EFFECTS OF OXIDATIVE STRESS USING N-ACETYLCYSTEINE

(75) Inventor: Francesco Santangelo, Milan (IT)

(73) Assignee: Zambon Group S.p.A., Vicenza (IT)

(*) Notice: Subject to any disclaimer, the term of this patent is extended or adjusted under 35 U.S.C. 154(b) by 0 days.

(21) Appl. No.: 09/926,363

(22) PCT Filed: Apr. 18, 2000

(86) PCT No.: PCT/EP00/03485
§ 371 (c)(1),
(2), (4) Date: Oct. 22, 2001

(87) PCT Pub. No.: WO00/64421
PCT Pub. Date: Nov. 2, 2000

(30) Foreign Application Priority Data

Apr. 21, 1999 (IT) .......................................... MI99A0831

(51) Int. Cl.$^7$ ............................................. A61K 31/195
(52) U.S. Cl. ....................................................... 514/562
(58) Field of Search ........................................ 514/562

(56) References Cited

FOREIGN PATENT DOCUMENTS

| EP | 0 836 534 | 5/1998 |
|----|-----------|--------|
| WO | 94/03169 | 2/1994 |
| WO | WO 98/34626 | 8/1998 |

OTHER PUBLICATIONS

A. G. Bostom, et al., Atherosclerosis, vol. 120, No. 1–1, pp. 241–244, "Lack of Effect of Oral N–Acetycysteine on the Acute Dialysis–Related Lowering of Total Plasma Homocysteine in Hemodialysis Patients", 1996.

T. Miyata, et al., The Journal of Clinical Investigation, vol. 98, No. 5, pp. 1088–1094, "The Receptor for Advanced Glycation End Products (RAGE) is a Central Mediator of the Interaction of Age–$\beta_2$Microglobulin With Human Mononuclear Phagocytes Via an Oxidant–Sensitive Pathway", 1996.

L. F. Prescott, Drugs, vol. 25, No. 3, pp. 290–314, "Paracetmol Overdosage Pharmacological Considerations and Clinincal Management", 1983.

M. Ruprah, et al., The Lancet, vol. 1, No. 8436, pp. 1027–1029, "Acute Carbon Tetrachloride Poisoning in 19 Patients: Implications for Diagnosis and Treatment", May 4, 1985.

M. G. Salom, et al., Transplantation, vol. 65, No. 10, pp. 1315–1321, "Protective Effect of N–Acetyl–L–cysteine on the Renel Failure Induced by Inferior Vena Cava Occlusion", May 27, 1998.

M. Damas Fernandez–Figares, et al., Farmacia Hospitalaria, vol. 16, No. 6, pp. 410–412, "Intoxicacion Accidental Por Administracion Rectal De Formaldehido", 1992.

M.E. Lund, et al., Clinical Toxicology, vol. 22, No. 1, pp. 31–49, "Treatment of Acute Methylmercury Ingestion by Hemodialysis with N–Acetylcysteine (Mucomyst) Infusion and 2,3–Dimercaptoropane Sulfonate", Jul. 1984.

A. E. Grzybowsky, Journal of Physiology and Pharmacology, vol. 50, No. 3, pp. 463–475, "In Vitro Effect of Glutathione Precursors on Cytotoxicity of Amino Acids to Human Mesothelial Cells", 1999.

J. Vadoud–Seyedi, et al., British Journal of Determatology, vol. 142, No. 3, pp. 580–581, "Treatment of Haemodialysis–Associated Pseudoporphyria with N–Acetylcysteine: Report of Two Cases", Mar. 2000.

M. Nakayama, et al., Peritoneal Dialysis International, vol. 19, No. 3, pp. 207–210, "Suppression of N$^e$–(Carboxymethyl)Lysine Generation by the Antioxidant N–Acetylcysteine", May 1999.

J. DiMari, et al., American Journal of Physiology, vol. 272, No. 3, Part 2, pp. F292–F298, "N–Acetyl Cysteine Ameliorates Ischemic Renal Failure", 1997.

Primary Examiner—Rebecca Cook
(74) Attorney, Agent, or Firm—Oblon, Spivak, McClelland, Maier & Neustadt, P.C.

(57) ABSTRACT

The present invention relates to methods of decreasing the effects of oxidative stress in patients undergoing hemodialysis by intravenously administering N-acetylcysteine or a pharmaceutically acceptable salt thereof to the patient.

21 Claims, 2 Drawing Sheets

METHODS OF DECREASING THE EFFECTS OF OXIDATIVE STRESS USING N-ACETYLCYSTEINE

This is a 371 of PCT/EP00/63485 filed Apr. 18, 2000.

The present invention relates to the use of N-acetylcysteine for intravenous administration in dialysed patients to prevent oxidative stress, which is responsible for the onset of numerous diseases.

The number of patients suffering from renal disease is constantly growing all over the world. The number of these patients starting with dialysis is growing too at a rate of 7–9% each year and it has been calculated that there will be more than 350,000 dialysed patients in the USA in 2010.

The hemodialysis procedure is usually carried out three times a week so totalling 156 times a year.

Recent studies have shown that hemodialysis is associated with oxidative stress (see for example the book "Haemodialysis and Oxidant Stress" Editors: Norbert Lameire, Gent; Ciro Tetta, Mirandola; Claudio Ronco, Vicenza—Reprint of "Blood Purification", vol. 17, No. 2–3, 1999).

Reactive oxygen species are generated as a consequence of cellular metabolism but the dialysis procedure causes a spontaneous and increased production of oxygen radicals. This phenomenon gives raise to several side effects such as lipid peroxidation, protein thiol group oxidation, DNA damage and release of proinflammatory molecules (for example cytokines) due to the oxidative stimulus.

From that, a number of noxious effects exerts such as anaemia, increased susceptibility to infections, accelerated atherosclerosis which has as a consequence the onset of cardiovascular diseases, the main cause of mortality in chronic dialysed patients (responsible for about half of all deaths). In particular, a high prevalence of vascular damages and of congestive heart failure has been observed.

N-acetylcysteine (hereinafter referred to as NAC) is a known drug (The Merck Index, XII ed., page 16, no. 89) used from decades in therapy, mainly as mucolytic.

Moreover, the detoxifying properties of NAC are widely known suggesting its use in the treatment of several pathologies, for example in the liver protection after intoxication from drugs such as paracetamol.

As for the treatment of patients undergoing dialysis, the oral administration of NAC has been recently described in the literature [Atherosclerosis 120 (1996) 241–244] to be without efficacy.

We have now surprisingly found that the preventive intravenous administration of NAC is able to decrease the effect of the oxidative stress in dialysed patients.

Therefore, object of the present invention is the use of NAC or pharmaceutically acceptable salts thereof for the preparation of a medicament suitable for the intravenous administration to prevent oxidative stress in dialysed patients.

Pharmaceutically acceptable salts of NAC which can be used according to the present invention are inorganic salts, preferably sodium salts.

NAC is preferably used.

The use of NAC or of its salts according to the present invention is a preventive use.

Then, NAC or its salts will be administered in a dosage form pharmaceutically suitable for the intravenous use, generally an aqueous solution, before and during the dialysis session, which generally lasts 3–5 hours.

The dose of NAC or of its salts to be administered for hemodialysis in acute renal disease treatment is generally from 100 to 200 mg/kg, preferably about 160 mg/kg.

The dose of NAC or of its salts to be administered for hemodialysis in the chronic treatment is generally from 500 to 5000 mg, preferably from 1 to 2 g.

In vitro Efficacy

The efficacy of NAC in preventing oxidative stress according to the present invention has been demonstrated in vitro by evaluating its effect on the presence of advanced oxidation protein products (AOPP), a marker of oxidative stress in the plasma of uremic patients (Witko-Sarsat V. et al., *The Journal of Immunology*, 1998, 161: 2524–2532), according to the following experimental procedure.

In vitro Preparation of AOPP

Human serum albumin (HSA) was exposed to HOCl at a molar HSA/HOCl molar ratio of 1/60. The AOPP-HSA preparation was incubated 30 minutes at room temperature and then dialysed overnight against PBS.

Isolation of Monocytes

Isolation of monocytes was performed by an indirect magnetic labelling system which allows the magnetic depletion of non monocytes i.e., T cells, B cells, NK cells, dendritic cells and basophils from a mononuclear cell suspension (obtained by blood sedimentation on a Ficoll gradient) using a cocktail of CD3, CD7, CD19, CD45RA, CD56 and anti-IgE antibodies. Purified monocytes were resuspended at a concentration of $2.5 \times 10^6$/ml in phenol-red free Hank's balanced salt solution (HBSS).

Isolation of Polymorphonuclear Neutrophils

Neutrophils from the Ficoll gradient pellet were separated from erythrocytes by sedimentation in dextran. Residual erythrocytes were lysed by treating the cell pellet with lysis buffer containing ammonium chloride. Purified neutrophils were resuspended at a concentration of $5 \times 10^6$/ml in phenol-red free HBSS at pH 7.4 and preincubated with medium alone or various concentrations of NAC.

Measurement of Monocyte and Neutrophil Oxygenation Activities

The capacity of AOPP-HSA to activate monocyte or neutrophil oxygenation activities was measured by chemiluminescence using dimethylbiacridinium (lucigenin) for NADH oxidase activity or luminol for myeloperoxidase activity as chemoluminogenic substrates. One hundred microliters of monocyte suspension ($2 \times 10^5$/ml) was automatically injected into the luminometer tubes containing 100 µl of HBSS (basal activity), or the tested preparations including: native HSA or AOPP-HSA at 2 mg/ml. Chemiluminescence production was measured in duplicate and luminescence intensity was expressed in counts/min integrated over a 40 minutes period.

Results

Figure 1A:
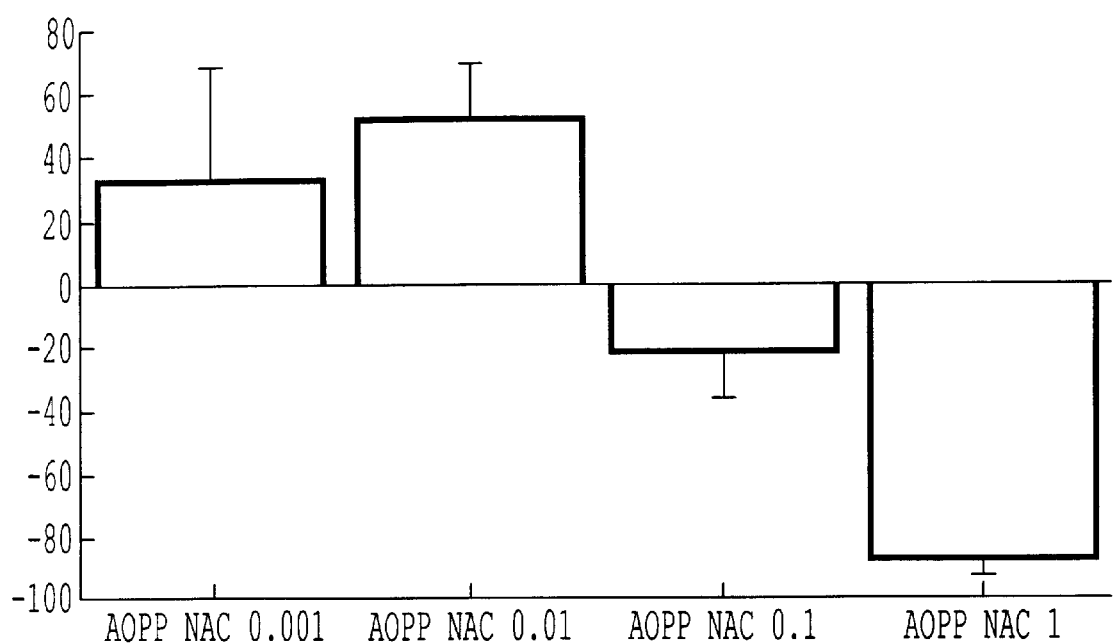
FIGS. 1A and 1B: The graphs depict the dose dependent effect of N-acetyl cysteine (NAC) on the presence of advanced oxidation protein products (AOPP)-induced myleoperoxidase oxygenation activity in neutrophils (A) and monocytes (B). The x-axis represents the amount of NAC tested and the y-axis is the luminescence in counts/min.
Figure 1B:
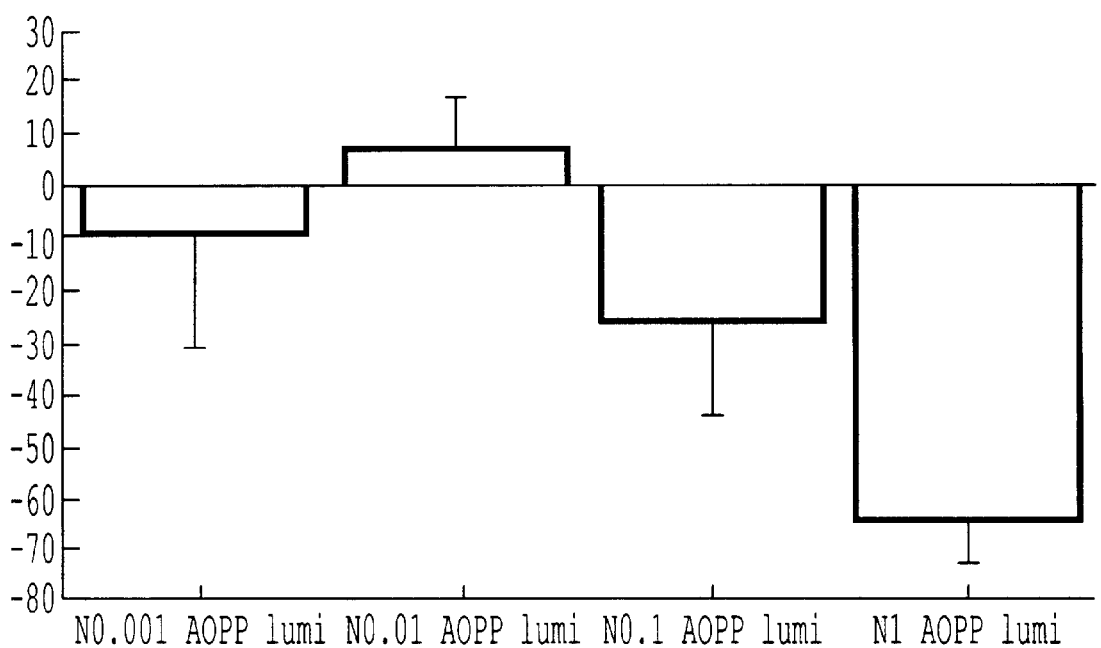
Figure 2A:
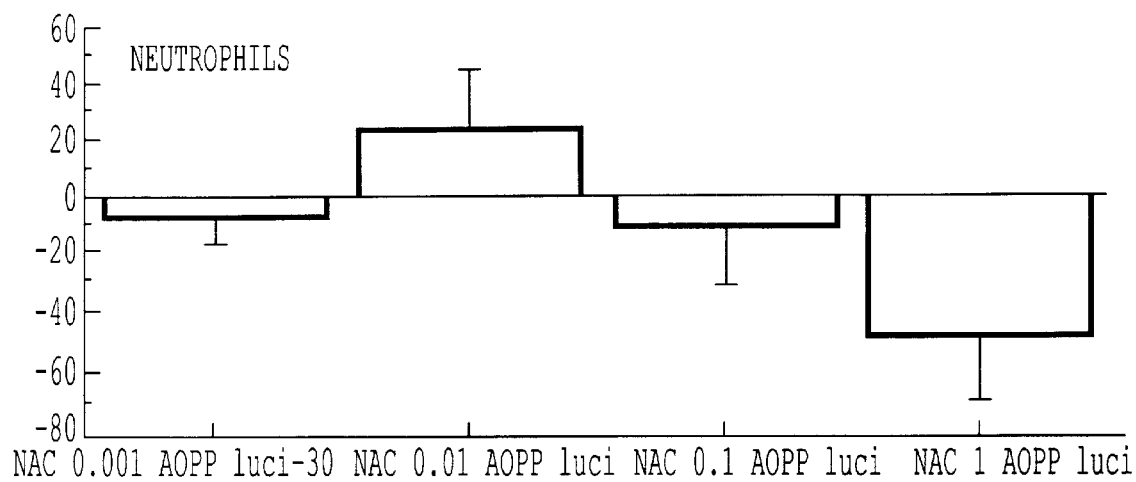
FIGS. 2A and 2B: The graphs depict the dose dependent effect of N-acetyl cysteine (NAC) on the presence of advanced oxidation protein products (AOPP)-induced NADPH-oxidase activity in neutrophils (A) and monocytes (B). The x-axis represents the amount of NAC tested and the y-axis is the luminescence in counts/min.
Figure 2B:
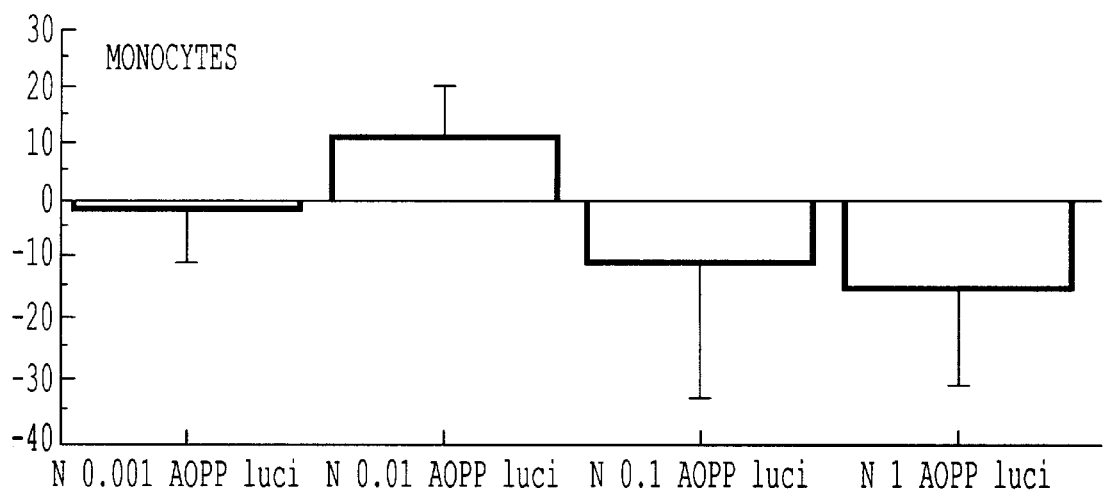

As compared to native HSA, AOPP-HSA triggered both monocytes and neutrophil NADPH oxidase and myeloperoxidase activities. NAC induced a dose-dependent inhibition of both NADPH oxidase and myeloperoxidase activities by AOPP-HSA in both monocytes and neutrophils as reported in the following FIGS. 1 and 2.

In vivo Efficacy

For the demonstration of the efficacy of NAC in preventing oxidative stress, according to the use object of the present invention, the following experimental protocol is followed.

Patients

Patients with prerenal or intrinsic acute renal failure requiring hemodialysis.

Dosage

NAC 40 mg/Kg as an i.v. loading dose (15 minutes) followed by 0.5 mg/Kg/minute as i.v. slow infusion during the entire hemodialysis session.

Treatment duration

Infusion lasting three to three and half hours during the second hemodialysis session.

Experimental design

Between-subjects comparison of hemodialysis alone and hemodialysis plus NAC carried out according to an entirely randomised study design. Open treatment with assessor blind procedure. Patients are evaluated during the second day of the hemodialysis treatment. Each patient remains under observation for three consecutive days: day one for general assessment, day two for study treatment, day three for follow-up observations 24 hours after the second hemodialysis session.

Efficacy assessment

The efficacy of NAC is evaluated by determining the following parameters:

a) Neutrophil phagocytic activity—measured, by flow cytometry, in whole blood after lysis of red blood cells.

b) NO production—spectrophotometrically detected in plasma as the sum of both nitrite and nitrate.

c) Ascorbyl radical—plasma (100 μl) is frozen immediately after separation and kept in liquid nitrogen (−176° C.) till measurement. Ascorbyl free radical is a stable free radical derived from the monooxidation of ascorbate and is measured directly using ESR (Electronic Spin Resonance) spectroscopy. The ESR spectrum of the ascorbyl free radical consists of a doublet identified by a g factor=2.0054 and by the characteristic hyperfine coupling constant $a^H$=1.88 G.

d) Inducible NO synthase (iNOS)—measured in PBMC, by direct measurement of the enzyme in Western Blotting. PBMC are isolated from the whole blood (2 ml) by Ficoll separation, PBMC proteins are extracted, separated by SDS-PAGE electrophoresis, and transferred on a membrane, where iNOS is immunodetected using an anti-iNOS monoclonal antibody. The complexes antibody-iNOS is revealed using a secondary antibody linked to an enzyme and measuring the activity of this enzyme.

e) Cytokine release ($TNF_\alpha$ plasma levels)—measured by enzyme-linked-immunosorbent assay (ELISA). The assay consists of a capture antibody anti-$TNF_\alpha$ attached to a microplate and a second antibody again anti-$TNF_\alpha$ attached to an enzyme. The concentration of $THF_\alpha$ is measured with a traditional enzyme assay.

From the evaluation of these parameters the efficacy of NAC in decreasing the oxidative stress in dialysed patients can be showed.

What is claimed is:

1. A method of decreasing the effect of oxidative stress in a patient, having renal disease undergoing chronic hemodialysis comprising administrating intravenously, during dialysis, N-acetylcysteine or a pharmaceutically acceptable salt thereof in an amount effective to decrease the effect of oxidative stress in said patient.

2. The method of claim 1, wherein N-acetylcysteine is administered.

3. The method of claim 1, wherein the sodium salt of N-acetylcysteine is administered.

4. The method of claim 1, wherein the amount is about 160 mg/kg.

5. The method of claim 1, wherein said patient is suffering from acute renal disease.

6. The method of claim 5, wherein the amount is from 100 to 200 mg/kg.

7. The method of claim 5, wherein the amount is from 500 to 5000 mg.

8. A method of decreasing the effect of oxidative stress in a patient having renal disease undergoing chronic hemodialysis comprising administrating intravenously, before dialysis, N-acetylcysteine or a pharmaceutically acceptable salt thereof in an amount effective to decrease the effect of oxidative stress in said patient.

9. The method of claim 8, wherein N-acetylcysteine is administered.

10. The method of claim 8, wherein the sodium salt of N-acetylcysteine is administered.

11. The method of claim 8, wherein the amount is about 160 mg/kg.

12. The method of claim 8, wherein said patient is suffering from acute renal disease.

13. The method of claim 12, wherein the amount is from 100 to 200 mg/kg.

14. The method of claim 12, wherein the amount is from 500 to 5000 mg.

15. A method of decreasing the effect of oxidative stress in a patient having renal disease undergoing chronic hemodialysis comprising administrating intravenously, before and during dialysis, N-acetylcysteine or a pharmaceutically acceptable salt thereof in an amount effective to decrease the effect of oxidative stress in said patient.

16. The method of claim 15, wherein N-acetylcysteine is administered.

17. The method of claim 15, wherein the sodium salt of N-acetylcysteine is administered.

18. The method of claim 15, wherein the amount is about 160 mg/kg.

19. The method of claim 15, wherein said patient is suffering from acute renal disease.

20. The method of claim 19, wherein the amount is from 100 to 200 mg/kg.

21. The method of claim 19, wherein the amount is from 500 to 5000 mg.

* * * * *